(12) United States Patent
Sheldon et al.

(10) Patent No.: US 9,353,367 B2
(45) Date of Patent: May 31, 2016

(54) NON-LEACHABLE MAGNETIC CROSS-LINKED ENZYME AGGREGATE

(75) Inventors: Roger Arthur Sheldon, Hoog Keppel (NL); Menno Jort Sorgedrager, Schipluiden (NL); Bernadett Kondor, Voorburg (NL)

(73) Assignee: CLEA TECHNOLOGIES B. V., Delft (NL)

( * ) Notice: Subject to any disclaimer, the term of this patent is extended or adjusted under 35 U.S.C. 154(b) by 628 days.

(21) Appl. No.: 13/808,357

(22) PCT Filed: Jul. 12, 2011

(86) PCT No.: PCT/NL2011/000054
§ 371 (c)(1),
(2), (4) Date: Mar. 18, 2013

(87) PCT Pub. No.: WO2012/023847
PCT Pub. Date: Feb. 23, 2012

(65) Prior Publication Data
US 2013/0196407 A1    Aug. 1, 2013

(30) Foreign Application Priority Data
Jul. 12, 2010   (NL) ..................................... 1038098

(51) Int. Cl.
*C12N 9/96* (2006.01)
*C12N 11/14* (2006.01)

(52) U.S. Cl.
CPC . *C12N 9/96* (2013.01); *C12N 11/14* (2013.01)

(58) Field of Classification Search
None
See application file for complete search history.

(56) References Cited

PUBLICATIONS

Lee et al., "Preparation of a magnetically switchable bio-electrocatalytic system employing cross-linked enzyme aggregates in magnetic mesocellular carbon foam", Angew. Chem. Int. Ed. 44: 7427-7432 (2005).*
Mavre et al., "Electrode surface confinement of self-assembled enzyme aggregates using magnetic nanoparticles and its application in bioelectrocatalysis", Anal. Chem. 79: 187-194 (2007).*
Kim et al., "A Magnetically Separable, Highly Stable Enzyme System Based on Nanocomposites of Enzymes and Magnetic Nanoparticles Shipped in Hierarchically Ordered Mesocellular, Mesoporous Silica", Small 1(12): 1203-1207 (2005).*

* cited by examiner

*Primary Examiner* — Anand Desai
(74) *Attorney, Agent, or Firm* — Troutman Sanders LLP; Ryan A. Schneider; Troy S. Kleckley

(57) ABSTRACT

A non-leachable, crosslinked, on a nanometer scale formed magnetic enzyme aggregate, consisting of a non-layered, hybrid nano-composite of functionalized magnetic nanoparticles and aggregated enzyme particles, is described. The magnetic enzyme aggregate can have a high enzyme content, of up to 99%. The high enzyme content allows the use on a small scale, such as for example in a fluidized bed, of the magnetic enzyme aggregate. Also, a process for the preparation of the present magnetic enzyme aggregate is described.

14 Claims, No Drawings

NON-LEACHABLE MAGNETIC CROSS-LINKED ENZYME AGGREGATE

BENEFIT CLAIMS

This application is a US National Stage of International Application No. PCT/NL2011/000054, filed 12 Jul. 2011, which claims the benefit of NL1038098, filed 12 Jul. 2010, both herein fully incorporated by reference.

FIELD OF THE INVENTION

Background of the Invention

The invention relates to a magnetic enzyme aggregate formed by chemical reaction, and more specifically to a non-leachable non-layered cross-linked magnetic enzyme aggregate.

It is observed that the expression magnetic is meant to indicate paramagnetic, superparamagnetic, ferromagnetic or ferrimagnetic behaviour, and thus includes compounds inherently having magnetic properties, as well as compounds which show magnetic properties under an applied magnetic field.

Functionalized (for instance amino, epoxy, aldehyde, isocyanate, alcohol, nitrile functionalised) magnetic nanoparticles for use as an alternative support material for enzymes have recently attracted much attention for the following reasons: when the size of the support material is decreased, for example to the nanometer scale, high surface areas can be obtained, so that more enzyme can be immobilized onto the particles; further, because of the magnetic properties of the magnetic nanoparticles, the immobilized enzyme can easily be controlled and recycled by the application of a magnetic field.

It is in this connection observed that, for distinguishing enzyme aggregates being bound to (or immobilized on) magnetic particles, the performance of the product is usually expressed as the Activity Recovery: this unit represents the activity of immobilisate as a percentage of the activity of the free enzyme used to make it.

A more relevant measure is nevertheless the Enzyme Loading, which is the amount of enzyme being present in a immobilisate as a percentage of the total weight of the sample. In fact, it is possible for a product to have a very high activity recovery, but at the same time have a very low enzyme loading.

From a practical point of view, it is thus important to have magnetic cross-linked enzyme aggregate with high enzyme loadings.

It is observed that cross-linked, magnetic enzyme-aggregates are as such known from several references.

J.-M Park et al., Process Biochemistry 45 (2010) 259-263, discloses cross-linked para-nitrobenzyl esterase of *Bacillus subtilis* aggregates on magnetic beads: this known product consists, more specifically, of a cross-linked enzyme aggregate which is immobilized onto magnetic beads. The size of the beads is on micrometer scale; beads having a diameter of 2.8 micrometer are used. It nevertheless appeared that the enzyme loading of this product is restricted to a maximum of about 3% w/w, which is an important limitation for such a product, although an activity recovery of 78% after immobilization was reported.

The use of magnetic nanoparticles for the immobilization of an enzyme is also known from Anal. Bioanal. Chem. (2004), 380: 606-613. This reference discloses a product consisting of magnetic nanoparticles that contained active $NH_2$ groups on their surface that were later used to attach the enzyme to the particles by using a cross-linking agent, by covalent coupling of the enzyme to the amino-modified magnetic nanoparticles. The nanoparticles used are nevertheless partly present as aggregates, which will lower the possible enzyme loading of the end product, while the enzyme is used as such, not as enzyme-aggregates.

Amino-functionalized magnetic nanoparticles, to which enzyme particles are bound, are also known from Process Biochemistry 44(2009) 1019-1024. The enzyme particles, which have not been aggregated, are, again, immobilized on the magnetic particles by covalent coupling. It is reported that, in use, and after 11 consecutive runs, the immobilized enzyme retained 59.6% of its initial activity.

The disadvantage of the prior art products—enzyme immobilized on magnetic particles—is the stability against leaching and low enzyme loading.

Further, Shao W. et al, Journal of Xi'an Jiatong University, vol. 42, no 8, August 2008, pages 1035-1039, mentions in the abstract that magnetic crosslinked enzyme aggregations were prepared by depositing of nuclease P1 with magnetic nanoparticles and crosslinked with glutaraldehyde. Only the optimal conditions of the used process are given, not the exact order of the different process steps. Further, there is talk of immobilisation, which suggests the formation of a layer of enzyme aggregates on the magnetic nanoparticles.

Cross-linked enzyme aggregates are, as such, known from EP-A-1.088.887, and are obtainable with the process comprising the steps of (i) treating an enzyme solution with the aid of a precipitating agent whereby aggregates are formed and precipitated, and (ii) subjecting the precipitate in situ to cross-linking with the aid of a cross-linking agent.

A product has now been found which obviates the disadvantages of the prior art products, i.e. has a high enzyme loading and is stable against leaching.

DETAILED DESCRIPTION OF PREFERRED EMBODIMENTS

The product according to the invention is more specifically a magnetic enzyme aggregate, which is thus non-leachable and has a high enzyme loading, and consists of a non-layered, hybrid, nano-composite of functionalised magnetic nanoparticles and pre-aggregated enzyme particles.

This product is different from the above-mentioned product in that the used enzyme-particles have been aggregated before being used in the present preparation process, and have not yet been cross-linked before being used. The use of functionalised, magnetic particles having nano sizes, then appeared to have the result that the enzyme particles are not immobilized onto the surface of the magnetic particles, but that the aggregated enzyme particles and magnetic nanoparticles have intimately, chemically, been reacted with each other to form a three-dimensional homogeneous composite. The component particles have thus reacted with each other on a nanometer scale.

In a preferred embodiment, the present composite consists of functionalised magnetic nanoparticles and aggregated enzyme particles being cross-linked with each other into a three-dimensional network, contrary to the layered structure of the prior art products.

Such a homogeneous cross-linked composite presents a very strong bond between the component particles, which prevents leaching of the enzyme particles and, even more important, makes it possible to obtain high enzyme loadings, and retains it.

It is observed that by magnetic particles, present in the composite according to the invention, paramagnetic, superparamagnetic, ferromagnetic or ferrimagnetic particles are understood. Such particles can be derived from, for example, $MoO_3$, $WO_3$, $Fe_3O_4$, and $TiO_2$, or suitable organic biradicals, which particles have properly been functionalised.

The functional groups, present on the magnetic nanoparticles are for instance amino, epoxy, aldehyde, isocyanate, alcohol, nitrile groups.

The combination of high enzyme loadings and nanoparticles, which inherently have a small weight, also allows the use of the present aggregates in a fluidised bed, if necessary by the application of a magnetic field to keep the aggregate particles in place.

The present composite is, according to a further possible embodiment, provided with a matrix former. Such an embodiment may be useful when the specific weight of the aggregate particles is low. In principle all insoluble matrix formers are suitable since only a surface, whether internal or external, is needed. Said matrix former can be a precursor of a compound usually known as a carrier or a filler. It is to be emphasized that the matrix former can also be a part of the three-dimensional homogeneous composite, which means in that case that it has also reacted with the magnetic nanoparticles and aggregated enzyme particles. When nevertheless said matrix former is added to the already formed magnetic enzyme aggregate of the invention, then some kind of encapsulation of the aggregate particles may take place. Such an embodiment also falls within the scope of protection of the present invention.

Suitable carriers are inorganic or organic, synthetic or natural carriers, consisting of the following components, such as acrylic polymers, activated carbon, agar, agarose, alginate, celite, cellulose, chitin, chitosan, DEAE-cellulose, gelatin, glass, hydroxyapatite, kieselguhr, latex beads, polyacrylamide, polypropylene, polystyrene, polyurethane, poly(vinyl alcohol), poly(vinyl chloride), polyvinylpyrrolidone, polyethyleneglycol, silica, Teflon, and derivatives of all these.

According to a further embodiment, the matrix consists of silica, preferably with amino groups activated silica. The preparation of such activated silica is as such known for an expert.

By adding a more hydrophobic or a more hydrophilic silica or silica precursor, it is possible to control the hydrophobicity of the produced enzyme aggregate. To control the particle size and/or hydrophobicity in the production process alkoxysilanes can be added; such compounds act as silica precursors. The alkoxysilanes are preferably selected from the group of $(MeO)_4Si$, $(EtO)_4Si$, $Me(MeO)_3Si$, and $propyl(MeO)_3Si$.

As already mentioned above, the enzyme loading of the present aggregate particles is high: The weight ratio of enzyme particles to magnetic nanoparticles in the aggregate particles is, according to a preferred embodiment of the invention, in the range from about 99:1 to about 20:80, more preferably from about 70:30 to 50:50, especially 50:50.

It is observed that such high enzyme loadings cannot be obtained when the enzyme particles are immobilized on the functionalised magnetic (nano-) particles, as discussed above.

Although the present composite shows good figures for the activity recovery, the inventor is of opinion that the enzyme loading of the composite is a more relevant characteristic to distinguish magnetic enzyme aggregates from each other, especially when the product is, or has been, used for several times as an enzyme preparation.

The invention further relates to a process for the preparation of a magnetic enzyme-aggregate, which is stable against leaching, wherein functionalised magnetic nanoparticles are cross-linked with aggregated enzyme particles in the presence of a cross-linking agent.

It is observed that the preparation of amino-functionalized magnetic nanoparticles is as such known, for example from the above mentioned paper from L. M. Rossi et al, in Anal. Bioanal. Chem. (2004) 380: 606-613. More specifically magnetite nanoparticles are first prepared, which are then reacted with 3-(aminopropyl)triethoxysilane to obtain the functionalised magnetic nanoparticles.

It is further observed that the preparation of aggregated enzyme particles is also as such known, and is effected by precipitation of the enzyme in solution using a precipitating agent to form insoluble enzyme aggregates. The term "enzyme aggregate" as such refers in the framework of the invention to any associated enzyme (or protein) particle obtained by any technique known by the expert.

Suitable enzymes preparations are, but not limited to, for instance penicilline acylases, lipases, esterases, epoxidehydrolases, amidases, aminopeptidases, nitrilases, nitrilehydratases, glycosidases, hydantoinases, or carbamoylases.

Another example of an envisaged application of the present invention is in the separation and reuse of the enzyme cocktail used in the breakdown of ligno cellulose to mono and oligosaccharides, in the pretreatment of lignocellulose prior to fermentation in second generation biofuels. The mixture obtained after the lignocellulose pretreatment consists of a complex slurry of liquid and solid fibre materials, which makes conventional solid/liquid separations to recover the biocatalyst impossible. Immobilization of this enzyme cocktail as a magnetic combi-CLEA, according to the invention, allows for facile magnetic separation of the biocatalyst from this complex slurry, and multiple reuse of the biocatalyst.

The precipitation, indicated above, is preferably performed at a temperature between 0 and 4° C. for reasons of stability, but can also be performed at room temperature, and is performed in a suitable buffer with a pH suitable for the enzyme of interest. In practice the pH will be between 4-11, preferably between 5-9. The precipitating agent is usually added stepwise and/or dissolved with constant stirring and pH control when needed. Addition of enzyme to precipitating agent is nevertheless also possible.

Suitable precipitating agents that can be used in the procedure of the present invention are in principle all water soluble precipitating agents that are used in the art of precipitation of biomolecules, for instance salts (organic or inorganic), organic solvents, (bio)polymers. It will be obvious that it is recommendable not to use precipitating agents that have a negative effect on enzyme stability. Some generally applicable and well known precipitating agents are quaternary ammonium salts or one of the other alkali metal salts, from the group of phosphate, sulfate, citrate, bicarbonate, carbonate, acetate, tartrate, succinate, chloride, and nitrate, or organic solvents like methanol, ethanol, propanol, isopropanol, butanol, and t-butylalcohol, or acetone, or any of the poly(ethylene glycol) (PEG) series. Preferably ammonium sulphate or a poly(ethylene glycol) (PEG) with a molecular weight preferably between 3000 and 16000 is used.

The amount of precipitating agent to be used is calculated with respect to the final volume and expressed as % of the saturation concentration when using initially solid precipitating agents like salts or a PEG series, whereas organic solvents are expressed as % v/v. The optimal amount of precipitating agent to be used is largely dependent on the specific precipitating agent chosen, and can easily be determined by the skilled person. For instance, the preferred amount of ammonium sulphate is 10 to 80% of the saturation concentration; the preferred amount of PEG is 20-50% (w/v) and of t-butyl alcohol is 50-70% (v/v). Preferably, if the precipitating agent is a salt it is used in a concentration up to its saturation concentration.

It is emphasised that the process according to the invention can be regarded as a cross-linking process between the magnetic nanoparticles and the aggregated enzyme particles. Applicant is of opinion that, because the magnetic particles and the enzyme particles have mainly the same, or almost the same, size, the particles behave like reagents, on a nanometer scale, and can therefore form a three-dimensional homogeneous network, which is comparable to a polymer network, contrary to the processes described in the prior art wherein there is talk of immobilization of the enzyme particles on the surface of the magnetic particles, probably because the magnetic particles are too large, or because the enzyme particles have already been cross-linked before the binding with the magnetic particles.

The magnetic nanoparticles are thus, according to the invention, incorporated and distributed in the aggregated enzyme system, and the aggregated enzyme system incorporated and distributed in the bulk of the magnetic nanoparticles, by a chemical binding reaction.

As indicated above, the functionalised magnetic nanoparticles are cross-linked with aggregated enzyme particles in the presence of a cross-linking agent.

The cross-linking agent can be bi- or polyfunctional.

Suitable cross-linking agents to be used are in principle all agents that can be used in the cross-linking of enzymes, such as an aldehyde, such as formaldehyde; dialdehydes, such as glyoxal and glutaraldehyde; polyaldehydes, such as dextran polyaldehyde; di-epoxides, such as diglycidylglycerol; polyamines, such as pentaethylene hexamine; diisocyanates, such as 1,6 hexamethylene diisocyanate; dinitril, such as 1,4 dicyanobutane. The preferred cross-linking agent is glutaraldehyde. It was shown that for penicillin acylase best results were obtained when a glutaraldehyde concentration of 0.5-4% (w/v) was used. However, the preferred glutaraldehyde concentration is 0.5-1% (w/v) calculated with respect to the final volume.

The cross-linking agent is preferably added to a solution of the mixture of enzyme aggregate and magnetic nanoparticles, and left for some appropriate time (for example 30 min to 18 hours). When the cross-linking reaction is finished, more water may be added to lower the viscosity of the mixture and the insoluble magnetic cross-linked enzyme (mCLEA) particles can be filtered or separated by any other method and extensively washed before being put in the final buffered solution for storage.

The aggregates according to the invention are for instance well suited to be employed in the enzymatic acylation of β-lactamnuclei to β-lactam antibiotics, in the enzymatic reactions in a fluidised bed, as biosensors, or in the enzymatic breakdown of lignocellulose to mono and oligosaccharides.

The invention is further explained with the following examples.

Example 1

Preparation of Magnetic *Candida antarctica* Lipase A Cross-Linked Enzyme Aggregate (Cal A mCLEA)

a. Synthesis of Amino Functionalised $Fe_3O_4$ Nanoparticles.

Magnetic iron nanoparticles were prepared by the precipitation of Fe(II) chloride and Fe(III) chloride. Fe(II) chloride ($FeCl_2 \times 4H_2O$) (0.994 g, 5 mml) and Fe(III) chloride ($FeCl_3 \times 6H_2O$) (2.7 g, 10 mmol) (Σiron ion=0.3 M) were mixed in 1:2 molar ratio in $dH_2O$ (50 mL) and precipitated by the addition of $NH_4OH$ at control pH 10-10.4 at 25° C. The particles were allowed to grow for 10 minutes. The suspension was stirred with a suspended glass stirrer. The magnetic nanoparticles were separated using a magnet and washed with $dH_2O$ 1× (50 mL) and 2-propanol 3× (50 mL). The particles were then resuspended in 250 mL 2-propanol and sonicated for 60 minutes. 3-aminopropyl triethoxysilane (APTES) was added to the nanoparticles suspension using a 1:1 molar ratio of $ATPES:Fe_3O_4$. The suspension was stirred with a suspended glass stirrer at room temperature overnight. The functionalised magnetic nanoparticles were separated using a magnet and washed with 2-propanol 2× (50 mL). The particles were then washed with acetone and dried under air.

b. Synthesis of Magnetic CLEAs 1 g amino functionalised nanoparticle was resuspended in 25 mL 2-propanol to which the enzyme solution of *Candida antarctica* lipase A (Cal A) (10 mL) was added dropwise and stirred at room temperature for 10 minutes. The cross-linker, glutaraldehyde (25% w/v aqueous) (350 µL) was added and the suspension was stirred at room temperature for 1 hour. Tetraethoxysilane (TEOS) (1 mL) and NaF (1 M, 180 µL) were added (first TEOS) and stirred at room temperature for 2 hours. TEOS (1 mL) and NaF (1 M, 180 µL) were added again and stirred at room temperature overnight.

The magnetic CLEAs were then separated using a magnet bar, washed 3 times with $H_2O$ (30 mL), and 3 times with acetone (20 mL) and resuspended in acetone (20 mL). The activity of the magnetic Cal A CLEA was determined by tributyrin hydrolysis.

Example 2

The advantages of magnetic enzyme aggregates according to the invention (called: mCLEA) compared to enzyme, immobilized on magnetic particles, demonstrated with lipase A from *Candida antarctica* (called: Cal A).

The technique to prepare magnetic CLEA (mCLEA) was shown to be advanced compared to the common immobilization technique used to produce immobilized enzyme on magnetic particles. The mCLEA is a homogeneous mixture of enzyme and magnetic particles while the common immobilization technique results in magnetic particles with a layer of enzyme on their surface.

It was shown (see tables 1 and 2) that the mCLEA, according to the invention, is superior in activity recovery, immobilization efficiency (100% immobilization efficiency: no active protein in the supernatant and wash—see tables 1 and 2), and stability (leaching) when compared to the magnetic immobilized *Candida antarctica* lipase A, as appears from the use of the two different preparation techniques.

TABLE 1

Magnetic cross-linked enzyme aggregate (mCLEA): composite of magnetic nanoparticles and aggregated enzyme particles. The results in the table are for mCLEA of *Candida antarctica* lipase A (Cal A mCLEA).

| E:NP (% w/w) | NP (mg) | Activity recovery of mCLEA (%)[i] | Activity of supernatant (%)[ii] | Activity of wash (%)[ii] | Leaching (%)[iii] |
|---|---|---|---|---|---|
| 85:15 | 1000 | 32 | 0 | 0 | 0 |
| 60:40 | 500 | 35 | 0 | 0 | 0 |
| 10:90 | 200 | 41 | 0 | 0 | 0 |

NP: nanoparticle - amount of functionalised nanoparticles in the mCLEA composite E: enzyme - amount of enzyme in the mCLEA composite

[i]AR %: activity recovery - percentage of activity of the mCLEA compared to the activity of the free enzyme

[ii]Activity % supernatant/wash: percentage of activity found in the supernatant/wash compared to the activity of the free enzyme

[iii]Leaching: percentage of activity compared to the activity of the mCLEA (see the description of the leaching experiment below)

TABLE 2

Enzyme on magnetic particles. The results in the table are for *Candida antarctica* lipase A immobilized on magnetic particles using amino functionalised nanoparticles activated with glutaraldehyde, enzyme bound via dialdehydes.

| E:NP (% w/w) | NP (mg) | Activity recovery of the immobilized enzyme (%)[i] | Activity of supernatant (%)[ii] | Activity of wash (%)[ii] | Leaching (%)[iii] |
|---|---|---|---|---|---|
| 5:95 | 1000 | 1.5 | 92 | 2 | 4 |
| 4:96 | 500 | 5 | 88 | 5 | 1 |
| 6:94 | 200 | 11 | 74 | 7 | 0.5 |

NP: nanoparticle - amount of functionalised nanoparticles in the immobilized enzyme
E: enzyme - amount of enzyme in the immobilized enzyme
[i]AR %: activity recovery - percentage of activity of the mCLEA compared to the activity of the free enzyme
[ii]Activity % supernatant/wash: percentage of activity found in the supernatant/wash compared to the activity of the free enzyme
[iii]Leaching: percentage of activity compared to the activity of the immobilized enzyme (see the description of the leaching experiment below)

The stability/leaching tests were executed as follows:

A known amount of mCLEA or immobilized enzyme (powder or suspension) was measured in a centrifuge tube, and 2 ml $dH_2O$ was added. The suspension was stirred with a magnetic stirrer bar for minimum 24 hours. The supernatant containing redissolved enzyme was separated and the activity was measured by tributyrin hydrolysis. The stability/leaching of the mCLEA or immobilized enzyme was calculated upon the activity found in the supernatant.

The invention claimed is:

1. Non-leachable, crosslinked, magnetic enzyme aggregate comprising:
   a hybrid, non-layered nanocomposite of functionalized magnetic nanoparticles and aggregated enzyme particles; and
   a matrix former;
   wherein said matrix former comprises a silica precursor, wherein said precursor is a silane compound.

2. The non-leachable, crosslinked, magnetic enzyme aggregate according to claim 1, wherein the functional groups of the magnetic nanoparticles are selected from the group consisting of amino, epoxy, aldehyde, isocyanate, alcohol, and nitril groups.

3. The non-leachable, crosslinked, magnetic enzyme aggregate according to claim 1, wherein the weight ratio from enzyme to nanoparticles in the aggregate is in the range from 99:1 to 20:80.

4. Non-leachable, crosslinked, magnetic enzyme aggregate comprising a hybrid, non-layered nanocomposite of functionalized magnetic nanoparticles and aggregated enzyme particles;
   wherein the enzyme comprises a combination of enzymes used in the breakdown of lignocellulose into mono and oligosaccharides.

5. A process for the preparation of a non-leachable, crosslinked, magnetic enzyme aggregate comprising a hybrid, non-layered nanocomposite of functionalized magnetic nanoparticles and aggregated enzyme particles, wherein functionalized magnetic nanoparticles are crosslinked with aggregated enzyme particles in the presence of a crosslinking agent at a temperature which is suitable for the aggregated enzyme particles, and wherein the functional groups of the magnetic nanoparticles are selected from the group consisting of amino, epoxy, aldehyde, isocyanate, alcohol, and nitril groups.

6. The process according to claim 5, wherein said crosslinking agent is a bi or polyfunctional crosslinking agent.

7. The process according to claim 5, wherein the reaction is executed in the presence of a matrix former.

8. The process according to claim 7, wherein said matrix former is silica.

9. A process for the preparation of a non-leachable, crosslinked, magnetic enzyme aggregate comprising a hybrid, non-layered nanocomposite of functionalized magnetic nanoparticles and aggregated enzyme particles, wherein functionalized magnetic nanoparticles are crosslinked with aggregated enzyme particles in the presence of a crosslinking agent at a temperature that is suitable for the aggregated enzyme particles;
   wherein the reaction is executed in the presence of a matrix former;
   wherein said matrix former comprises a silica precursor; and
   wherein said precursor is a silane compound.

10. The process according to claim 9, wherein said silane compound is selected from the group consisting of tetraethoxy silane, tetramethoxy silane, methyl trimethoxy silane, and propyl trimethoxy silane.

11. The process according claim 5, wherein the weight ratio from aggregated enzyme particles to nanoparticles is in the range from 99:1 to 20:80.

12. A process for the preparation of a non-leachable, crosslinked, magnetic enzyme aggregate comprising a hybrid, non-layered nanocomposite of functionalized magnetic nanoparticles and aggregated enzyme particles, wherein functionalized magnetic nanoparticles are crosslinked with aggregated enzyme particles in the presence of a crosslinking agent at a temperature that is suitable for the aggregated enzyme particles;
   wherein the reaction is executed in the presence of a matrix former; and
   wherein the enzyme is used in the breakdown of lignocellulose into mono and oligosaccharides.

13. Non-leachable, crosslinked, magnetic enzyme aggregate comprising:
   a hybrid, non-layered nanocomposite of functionalized magnetic nanoparticles and aggregated enzyme particles; and
   a matrix former;
   wherein the functional groups of the magnetic nanoparticles comprise amino groups;
   wherein the matrix former comprises silica with amino groups activated silica, or a precursor thereof;
   wherein if the matrix former comprises a silica precursor, the precursor is a silane compound selected from the group consisting of an alkoxysilane compound, tetramethoxy silane, tetraethoxy silane, methyl trimethoxy silane, and propyl trimethoxy silane;
   wherein the enzyme is used in the breakdown of lignocellulose into mono and oligosaccharides; and
   wherein the weight ratio from enzyme to nanoparticles in the aggregate is 50:50.

14. A process for the preparation of a non-leachable, crosslinked, magnetic enzyme aggregate comprising a hybrid, non-layered nanocomposite of functionalized magnetic nanoparticles and aggregated enzyme particles, wherein functionalized magnetic nanoparticles are crosslinked with aggregated enzyme particles in the presence of a crosslinking agent at a temperature that is suitable for the aggregated enzyme particles;

wherein the functional groups of the magnetic nanoparticles comprise amino groups;
wherein said crosslinking agent comprises glutaraldehyde;
wherein the reaction is executed in the presence of a crosslinkable matrix former comprising tetraethoxy silane;
wherein the weight ratio from enzyme to nanoparticles in the aggregate is 50:50; and
wherein the enzyme comprising a combination of enzymes used in the breakdown of lignocellulose into mono and oligosaccharides.

* * * * *